United States Patent [19]

Liang

[11] Patent Number: 5,502,234
[45] Date of Patent: Mar. 26, 1996

[54] PROCESS FOR THE PREPARATION AND SEPARATION OF CYCLOPROPANECARBONITRILE

[75] Inventor: Shaowo Liang, Kingsport, Tenn.

[73] Assignee: Eastman Chemical Company, Kingsport, Tenn.

[21] Appl. No.: 503,345

[22] Filed: Jul. 17, 1995

[51] Int. Cl.$^6$ .................................................... C07C 253/00
[52] U.S. Cl. ............................................ 558/314; 558/434
[58] Field of Search ..................................... 558/314, 434

[56] References Cited

U.S. PATENT DOCUMENTS

| | | | |
|---|---|---|---|
| 4,235,807 | 11/1980 | Fuhlhage | 558/314 |
| 4,686,302 | 8/1987 | Merger et al. | 558/314 |
| 5,349,103 | 9/1994 | Gülec | 518/434 |
| 5,380,911 | 1/1995 | Strong | 558/434 |

OTHER PUBLICATIONS

T. ven Es, (J. Chem. Soc.) 1965, p. 1564.
G. A. Olah et al. Synthesis (1979) pp. 112–113.

*Primary Examiner*—Joseph Paul Brust
*Attorney, Agent, or Firm*—J. Frederick Thomsen; Harry J. Gwinnell

[57] ABSTRACT

Disclosed is a novel process for the preparation and separation of cyclopropanecarbonitrile (CPCN) from cyclopropanecarboxaldehyde (CPCA) using a combination of three process steps. The process involves the steps of (1) reacting (CPCA) with hydroxylamine base in the presence of water to obtain CPCA oxime, (2) contacting the CPCA oxime of step (1) with formic acid to obtain CPCN, and (3) contacting the mixture comprising CPCN formed in step (2) with a base to obtain a mixture comprising an organic phase containing CPCN and an aqueous phase. The reactants and intermediates involved in each step are used within certain defined ratios.

8 Claims, No Drawings

PROCESS FOR THE PREPARATION AND SEPARATION OF CYCLOPROPANECARBONITRILE

This invention pertains to a novel process for the preparation and separation of cyclopropanecarbonitrile (CPCN) from cyclopropropanecarboxaldehyde (CPCA). More specifically, this invention pertains to a combination of process steps whereby CPCA is converted to its oxime, the oxime is converted to CPCN and the nitrile product is obtained from the reaction mixture as a separate organic phase. The process provided by the present invention results in the formation and recovery of CPCN in good selectivities and yields.

CPCN has proven to be a valuable as well as versatile compound. For example, it is an important synthetic building block for introducing the cyclopropane ring into agricultural chemicals such as N-cycloalkylanilines, whose performance characteristics are substantially improved by the presence of the cyclopropyl group.

Prior art methods for preparing CPCN have involved reacting, in general, a halobutyronitrile with a base such as alkali metal hydroxide (*J. Am. Chem. Soc.*, 1927, 49, 2066 and *J. Am. Chem. Soc.*, 1929, 51, 1174) or sodium amide (*J. Am. Chem. Soc.*, 1941, 63, 1734). However, certain problems have been encountered with these prior art procedures. For example, high temperatures normally are required for these reactions. Furthermore, substandard yields of product frequently have been obtained due to troublesome side reactions and as well as to difficult and prolonged distillation procedures.

U.S. Pat. No. 3,853,942 describes a process for the preparation of CPCN by reacting halobutyronitrile with an alkali metal alkoxide in an inert solvent at elevated temperatures and removing the alcohol formed. However, the alkali metal alkoxide is a relatively expensive reactant which is also difficult to handle. U.S. Pat. No. 4,205,009 and GB 1,570,319 describe a similar process using alkali metal hydroxide instead of alkoxide in the presence of an anionic surfactant and an inert organic solvent. However, for better control of this phase transfer reaction, environmentally unfriendly solvents such as benzene or dichloromethane are required.

Furthermore, 4-halobutyronitrile (4-chloro and 4-bromobutyronitrile in particular) is used as the starting material in all of the prior art procedures. Methods for preparing such nitriles are described in *J. Am. Chem. Soc.* articles and U.S. Pat. No. 3,853,942 noted hereinabove. These nitriles are typically prepared by the anhydrous, free radical reaction of allyl chloride and hydrogen halide in the presence of benzoyl peroxide followed by the reaction of the resulting trimethylenechlorohalide, in 50% excess, with sodium cyanide in ethanol-water medium. These chemical transformations require the handling of a corrosive hydrogen halide and a highly toxic metal cyanide. Formation of regioisomers in these steps resulted in complications in product isolation.

Additional procedures for the synthesis of CPCN on a laboratory scale are described by a carbene insertion or Simmons-Smith reaction with acrylonitrile (see, for example, M. Mitain, et al., *J. Chem. Soc., Chem Commun.*, 1983, 1446; H. Kanai, et al. Bull. *Chem. Soc. Jpn.* 1983 56, 1025) or by dehydration of cyclopropanecarboxamide with the liquid "diphosgene", trichloromethyl chloroformate as dehydrating agent (K. Mai and G. Patil, *Tetrahedron Lett.*, 1986, 27, 2203). While convenient for laboratory use, these procedures present serious safety concerns and/or require the use of expensive reagents when utilized on a commercial scale. Prior art methods for preparing carbonitriles from aldehydes have involved, in general, (a) dehydration of aldoximes using diclohexylcarbodiimide, N,N'-carbonyldiimidazole, N,N-dimethyldichloromethaniminium chloride, phosphonitrile dichloride, phenylchlorosulfite or selenium dioxide; (b) 1,2-elimination of reactions of O-substituted aldoximes; (c) 1,2-elimination reactions of aldehyde trimethylhydrazonium iodides and aldehyde N-tosylimines using base; (d) conversion of aldehydes to nitriles using, ammonia/sodium methoxide in methanol containing iodine or using an amine imide as an oxidizing agent. While convenient for laboratory use, these methods are not suitable for large-scale commercial use due primarily to safety concerns and/or the use of expensive reagents.

Finally, aldehydes having the formula R—CHO have been converted to nitriles having the formula to R—CN, wherein R is aryl or acyclic alkyl, using hydroxylamine hydrochloride with large quantity of formic acid as solvent in the presence or absence of sodium formate. This method can give reasonable yields and less side reactions when R is an aromatic moiety or a long aliphatic chain. For example, T. ven Es, (*J. Chem. Soc.* 1965, 1564) describes a procedure of using 1.15 equivalents of hydroxylamine hydrochloride and excess sodium formate (2 equivalents) with large amounts of formic acid (33 equivalents) to give good yields of aromatic nitriles. However the procedure gives very poor selectivity for the conversion of n-butyraldehyde to butyronitrile (30% yield). Preparation of cyclopropanecarbonitrile is not mentioned. G. A. Olah and T. Keumi (*Synthesis* 1979, 112) describe a similar procedure (except no sodium formate is used) for the synthesis of aromatic nitriles and selected acyclic alkylnitriles. In order to dissolve the hydroxylamine salt completely and to minimize side reactions, large amounts, e.g., 22 equivalents, of formic acid are required. It is very difficult, if it is not impossible, to isolate lower alkyl nitriles, e.g., nitriles containing a total of 2 to 4 carbon atoms, from formic acid either by extraction or by distillation (formation of azeotrope). Neutralization with a base (5% aqueous sodium hydroxide solution), according to the Olah et al. procedure, generated more than 20 equivalents of Salts as wastes. Very intensive extractions are required for the product recovery of aliphatic nitriles. It is apparent that the commercial-scale use of the procedure described by Olah et al. would present serious problems.

A process now has been developed for the production of CPCN from CPCA in high selectivity and yield and for the recovery of the nitrile product by procedures which may be carried out satisfactorily on a commercial scale. The process of the present invention provides a means for the preparation and separation of CPCN by the steps comprising:

(1) reacting CPCA with hydroxylamine base in the presence of water to obtain CPCA oxime, wherein the mole ratio of CPCA:hydroxylamine is about 1:0.5 to 1:5;

(2) contacting the CPCA oxime of step (1) with formic acid to obtain CPCN, wherein the mole ratio of formic acid:CPCA oxime is about 0.5:1 to 5:1; and (3) contacting the mixture comprising CPCN formed in step (2) with a base to obtain a mixture comprising an organic phase containing CPCN and an aqueous phase, wherein the equivalents of base per mole formic acid used in step (2) is in the range of about 0.5:1 to 2:1. Most, e.g., up to 90 weight percent, of the CPCN formed is obtained in the organic phase formed in step (3). This crude product may be refined by distillation to obtain CPCN having a purity of 99% or greater. Alternatively, the crude product may be used-without purification in the synthesis of other compounds, e.g., the crude CPCN may be catalytically hydrogenated to produce cyploroylmethylamine.

The starting material for the present process, CPCA, may be obtained by the thermal rearrangement of 2,3-dihydrofuran. For example, U.S. Pat. No. 4,275,238 describes passing 2,3-dihydrofuran through a column at 480° C. to obtain CPCA having a purity of 90% purity and containing 6.2–6.7% crotonaldehyde. A similar procedure is described by Wilson (*J. Amer. Chem. Soc.* 1947, 69, 3002). 2,3-Dihydrofuran may be obtained according to the process described in U.S. Pat. No. 5,254,701 by the isomerization of 2,5-dihydrofuran which in turn can be produced by the isomerization of 3,4-epoxy-1-butene as described in U.S. Pat. Nos. 3,932,468, 3,996,248 and 5,082,956. U.S. Pat. Nos. 4,897,498 and 4,950,773 describe the preparation of 3,4-epoxy-1-butene by selective monoepoxidation of butadiene.

The hydroxylamine base employed in the first step of the process of this invention may be used in the form of a 10 to 50, preferably 50, weight percent solution in water. Alternatively, the hydroxylamine base can be as generated in situ by treating an acid salt of hydroxylamine with a base such as an alkali metal hydroxide, preferably sodium hydroxide. Hydroxylamine salts include salts which hydroxylamine forms with inorganic acids such as sulfuric acid, hydrochloric acid, nitric acid, and phosphoric acid or with organic acids such as formic acid, acetic acid, propionic acid, and sulfonic acids. Examples of these hydroxylamine salts include hydroxylamine sulfate, hydroxylamine hydrochloride, hydroxylamine phosphate, hydroxylamine nitrate and hydroxylamine formate, etc. When a hydroxylamine salt is used in step (1), the hydroxylamine salt is dissolved in water followed by neutralization with an alkali metal hydroxide, preferably sodium hydroxide, to generate hydroxylamine base. The concentration of the hydroxylamine salt in the hydroxylamine salt aqueous solution may range from about 10 to 70 weight percent, preferably 30 to 50 weight percent.

The advantage of using hydroxylamine free base (either as an aqueous solution or generated in situ from its salt) is to avoid the generation of strong acids during the oxime formation when hydroxylamine acid salts are used. Such acids typically cause side reactions such as, for example, ring cleavage by HCl to give 4-chlorobutyronitrile, Beckmann rearrangement to give cyclopropanecarboxamide and strong acid-catalyzed hydrolysis of the product nitrile to the corresponding carboxamide and/or carboxylic acid. It is known that oximes of lower alkyl aldehydes, e.g. $C_2$–$C_4$ aldehydes, such as acetaldehyde (J. B. Chattopadhyaya, and A. V. Rama Rao, *Tetrahedron* 1974, 30, 2899), propionaldehyde and butyraldehyde (J. P. De Keersmaeker, and F. Fontyn, *Ind. Chim. Belge,* 1967, 32, 1087) mainly form the corresponding amides via Beckmann rearrangement under acid-catalyzed conditions. It is well known that nitriles, especially lower alkyl nitriles readily undergo hydrolysis in the presence of strong acids such as sulfuric acid and hydrochloric acid (*J. Amer. Chem. Soc.* 1952, 74, 694; W. Wenner, Org. Synth. 1952, 32, 92).

In step (1) of the process, aqueous hydroxylamine solution is contacted with CPCA at a temperature of less than about 120° C., preferably about 5° to 80° C. to produce CPCA oxime. The mole ratio of CPCA:hydroxylamine is about 1:0.5 to 1:5, preferably about 1:1 to 1:1.2. At the conclusion of step (1), some of the water present in the reaction mixture may be removed, depending in part upon the concentration of the hydroxylamine base used in step (1) and the materials and/or amounts thereof used in steps (2) and (3). Generally, when the hydroxylamine free base is used as an aqueous solution in a concentration of less than about 40 weight percent, some of the water present in the reaction mixture is removed, e.g., at least 40 weight percent, and preferably at least 80 weight percent, of the water is removed. The removal of water can favorably affect reaction rates in steps (2) and (3) and separation of the CPCN product. Conversely, when hydroxylamine concentrations greater than 40 weight percent in water are used, removal of water is less advantageous.

When the hydroxylamine base is generated in situ as described above, the CPCA oxime produced forms a separate organic phase which normally is separated from the aqueous solution containing one or more alkali salts. Optionally, the CPCA oxime can be isolated by crystallization after removal of most of the water and cooling. However, such isolation of solid CPCA oxime is not involved in the 3-step process of the present invention.

In the second step of the process, formic acid and the CPCA oxime-containing material from step (1) are contacted at a temperature of about 50° to 150° C., preferably 80° to 120° C., for a period of time to ensure complete consumption of the CPCA oxime to produce CPCN as the primary product. The amount of formic acid used in step (2) should give a formic acid:CPCA oxime mole ratio of about 0.5:1 to 5:1, preferably 0.7:1 to 3:1, and most preferably 0.7:1 to 1.2:1. Although the use of low amounts (relative to the teachings of the prior art) of formic acid require the use of longer reaction times, such use of lower amount of formic acid is an important feature of the present invention to permit the convenient separation of the product CPCN. The purity or concentration of the formic acid used typically is at least 80 weight percent and preferably at least 90 weight percent.

In the third step of the process, the material (containing CPCN and formic acid) resulting from step (2) is contacted with a base to obtain a mixture comprising an organic phase containing CPCN and an aqueous phase. Most, e.g., up to 98 weight percent, of the CPCN formed is obtained in the organic phase formed in step (3). Step (3) normally is carried out at a temperature of less than about 75° C., preferably in the range of about 30° to 55° C. Examples of the bases which may be used in the third step include the alkali metal hydroxides and carbonates and the alkaline earth metal hydroxides and carbonates. The hydroxides and carbonates of sodium, potassium, cesium, magnesium and calcium are specific examples of bases useful in step (3). The alkali metal hydroxides and, especially, sodium hydroxide represent the most preferred bases.

The amount of base utilized in step (3) typically gives an equivalent of base per mole of formic acid used in step (2) of about 0.5:1 to about 2:1, preferably about 0.8:1 to 1.2:1. The term "equivalent" is used herein to specify the stoichiometric amount of base required to neutralize 1 mole of formic acid. For example, a mole of alkali metal hydroxide constitutes 1 equivalent of base whereas 1 mole of alkali metal carbonates and alkaline earth metal hydroxides and carbonates constitutes 2 equivalents of base. Although the base can be used in step (3) in the form of a finely divided solid, it more conveniently is used as an aqueous solution, e.g., in base concentrations of up to 90 weight percent, depending upon the particular base used. The concentration of the preferred alkali metal hydroxides in the aqueous alkali metal hydroxide solutions preferably is about 40 to 60 weight percent. A 50 weight percent aqueous sodium hydroxide solution is the most preferred alkali metal hydroxide solution.

The organic layer of the two-phase mixture resulting from step (3) can be isolated by known recovery procedures. As mentioned above, it is possible to use the crude CPCN contained in the organic phase without further purification. Normally, however, the CPCN-containing phase is purified, e.g., by distillation, prior to the conversion of the CPCN to other chemical compounds. The aqueous phase of the step (3) mixture can be extracted with a suitable water-immiscible solvent to recover addition CPCN. Examples of suitable water-immiscible extractants include tertiary butyl methyl ether, diethyl ether, diisopropyl ether, alkyl acetates such as propyl and isopropyl acetate, toluene, benzene, diethoxymethane and alkyl nitriles such as acetonitrile and butyronitrile.

It will be apparent to those skilled in the art that the process described herein provides a simple and convenient means for the preparation and separation of CPCN form CPCA. The process of the present invention provides an economical procedure for the production of CPCN which eliminates the use of expensive reagents and highly toxic materials which are difficult to handle. The process of this invention may be carried out in a single reactor or "pot" using mild conditions while generating a limited amount of waste. None of the prior art references discussed herein teaches a process for the preparation of a nitrile wherein the nitrile product is separated and recovered as a liquid, organic phase.

Another advantage provided by the process of this invention is that high purity CPCA is not required for the production of CPCN. For example, CPCA containing 5 to 15 weight percent crotonaldehyde typically is obtained by the thermal isomerization of 2,3-dihydrofuran. When such CPCA/crotonaldehyde mixtures are utilized in the present process, the crotonaldehyde is completely converted to high boilers. No crotonitrile formation is observed during the preparation of CPCN. Essentially pure CPCN can be obtained by distillation after the usual work up.

The process provided by the present invention is further illustrated by the following examples. Gas chromatographic (GC) analyses were performed on a Hewlett-Packard 5890 series II gas chromatography with a 30 meter DB-Wax and a 30 meter DB-17 capillary columns. The identities of the products obtained were confirmed by nuclear magnetic resonance spectrometry and gas chromatography-mass spectrometry by comparison to authentic samples purchased from Aldrich Chemical Company.

EXAMPLE 1

CPCA (98% assay, 357 g, 5 mol) was added to a two-liter, three-necked flask containing 50% aqueous hydroxylamine solution (363 g, 5.5 mol) while maintaining the temperature below 50° C. with an external water bath. Upon completion of the CPCA addition, GC analysis showed complete formation of CPCA oxime (cis and trans isomers). The mixture was heated at 100°–120° C. and water (246 g) was distilled out through a 40 cm column containing Penn State packing material.

The mixture was cooled to 70°–80° C. and formic acid (95%, 242 g, 5 mol) was added. The resulting mixture was refluxed for 3 hr. The reaction mixture (714 g) was cooled to room temperature and GC analysis indicated the formation of CPCN (314.5 g, 93.9% yield) and cyclopropanecarboxamide (8.5 g) which demonstrated that the selectivity of the conversion of CPCA to CPCN compared to the conversion of CPCA to cyclopropanecarboxamide is 97.9%.

To the product mixture was added 50 weight percent aqueous sodium hydroxide solution (400 g, 5 mol) while maintaining the temperature below 35° C. The resulting mixture separated into two phases. The organic phase (349.2 g) was separated and analysis showed that it contained 88.2% (308 g) CPCN. The aqueous phase was extracted with tert-butyl methyl ether (t-BuOMe, 100 g) to give 96 g organic solution containing 5.72% (5.5 g) CPCN. The total yield after work up was 313.5 g CPCN (93.6% yield). Distillation of the combined organic phases gave 304.6 g CPCN having a purity exceeding 99%.

EXAMPLE 2

CPCA (92% assay, contains 7% crotonaldehyde, 350 g, 4.6 mol) was added over a period of 30 minutes to a one-liter, three-necked flask containing 50 weight percent aqueous hydroxylamine solution (345 g, 5.23 mol). After the completion of the addition of CPCA, GC analysis showed complete formation of CPCA oxime (cis and trans isomers). The mixture was heated at 100°–120° C. and water (210 g) was distilled from the mixture through a 30 cm column containing Penn State packing.

The mixture was cooled to 70°–80° C. formic acid (95%, 167 g, 3.45 mol) was added and the resulting mixture was refluxed for 5 hour. The reaction mixture (652 g) was cooled to room temperature and GC analysis indicated the formation of CPCN (269.6 g, 87.5% yield) and cyclopropanecarboxamide (17.3 g) which demonstrated that the selectivity of the conversion of CPCA to CPCN compared to the conversion of CPCA to cyclopropanecarboxamide is 95.2%.

To the CPCN-containing reaction mixture was added 50 weight percent aqueous sodium hydroxide solution (275 g 3.44 mol) while maintaining the temperature below 35° C. The resulting mixture separated into two phases. The organic phase (303.7 g) was separated and analysis showed that it contained 86.55% (262.9 g) CPCN. The aqueous phase was extracted with t-BuOMe (100 g) to give 101.2 g solution containing 5.72% (5.8 g) CPCN. The total yield after work up was 268.7 g CPCN (87.2% of theory). Distillation of the combined organic phases gave CPCN having a purity greater than 99%.

EXAMPLE 3

CPCA (92% assay contains 7% crotonaldehyde, 210 g, 2.76 mol) was added over a period of 30 minutes to a one-liter, three-necked flask containing 50% aqueous hydroxylamine solution (207 g, 3.14 mol). After the addition of CPCA was complete, GC analysis showed complete formation of CPCA oxime (cis and trans isomers). The resulting mixture was used in the second step without removing any water.

To the mixture containing CPCA oxime was added 95% formic acid (100 g, 2.07 mol) and the resulting mixture was refluxed for 8 hours. The reaction mixture (513.3 g) was cooled to room temperature and GC analysis indicated the formation of CPCN (156.18 g, 84.46% yield) and cyclopropanecarboxamide (14.53 g) which demonstrated that the selectivity of the conversion of CPCA to CPCN compared to the conversion of CPCA to cyclopropanecarboxamide is 93.2%.

To the CPCN-containing reaction mixture was added 50% sodium hydroxide (165 g, 2.07 mol) while maintaining the temperature below 30° C. The resulting mixture separated into two phases. The organic phase (178.5 g) was separated and analysis showed that it contained 82.85% (147.9 g) CPCN. The aqueous phase was extracted with t-BuOMe (77.7 g) to give 79.23 g of an organic solution containing 8.74% (6.9 g) CPCN. The total yield after work up was 154.8 g CPCN (83.7% of theory). Distillation of the combined organic phases gave CPCN having a purity greater than 99%.

EXAMPLE 4

50% Sodium hydroxide (176 g, 2.2 mol) was added dropwise to a one-liter, three-necked flask containing a solution of hydroxylamine sulfate (180.57 g, 1.1 mol) in water (200 g) while maintaining the temperature below 35° C. with a water cooling bath. To the resulting solution containing hydroxylamine base was added CPCA (98% assay 143 g, 2.0 mol) over a period of 5 minutes Upon completion of the CPCA addition, the mixture separated into two phases. Analysis of the organic phase showed that formation of CPCA oxime was complete. The aqueous phase was discarded.

Formic acid (95%, 96 84 g, 2.0 mol) was added to the CPCA oxime organic phase and the resulting mixture was refluxed (110°–120° C.) for 3 hours. The mixture was cooled to room temperature and 50% sodium hydroxide (160 g, 2.0 mol) was added while maintaining the temperature below 50° C. The resulting mixture separated into two phases. The organic phase (137 g) was separated and analysis showed that it contained 86.58% (118.61 g) CPCN. The aqueous phase was extracted with t-BuOMe (50 g) to give 48 g of a solution containing 7.36% (3.53 g) CPCN. The total yield after work up was 122.14 g CPCN (91.15% of theory). Distillation of the combined organic phases gave 116.3 g CPCN having a purity exceeding 99%. Based on GC analysis, the total amounts of by-product cyclopropanecarboxamide formed was 2.59 g which indicates that the selectivity of the conversion of CPCA to CPCN compared to the conversion of CPCA to cyclopropanecarboxamide is 98.4%.

EXAMPLE 5

50% Sodium hydroxide (160 g, 2.0 mol) was added dropwise (about 15 minutes) to a one-liter, three-necked flask containing a solution of hydroxylamine sulfate (164.15 g, 1 mol) in water (300 g) while maintaining the temperature below 30° C. with a ice-water cooling bath. To the resulting solution was added CPCA (90% assay, contains 8% crotonaldehyde, 140 g, 1.8 mol) over a period of 5 minutes. The mixture was stirred at room temperature for 20 minutes and then it was allowed to separate into two phases. GC analysis showed that CPCA oxime formation was complete. The upper organic phase was separated from the lower aqueous phase.

Formic acid (95%, 67.8 g, 1.4 mol) was added to the organic phase and the resulting mixture was refluxed for 5 hours. The mixture was cooled to room temperature and 50% sodium hydroxide (112 g, 1.4 mol) was added while maintaining the temperature below 35° C. The resulting mixture separated into two phases. Analysis of the organic phase (125 g) showed that it contained 77.87% (97.34 g) CPCN. The aqueous phase was extracted with t-BuOMe (35 g) to give 32 g of an extract solution containing 6.09% (1.95 g) CPCN. The total yield after work up was 99.3 g CPCN (82.3% of theory). Distillation of the combined organic phases gave CPCN having a purity of 99%. Based on GC analysis, the total amounts of by-product cyclopropanecarboxamide formed was 4.46 g which shows that the selectivity of the conversion of CPCA to CPCN compared to the conversion of CPCA to cyclopropanecarboxamide is 96.6%.

EXAMPLE 6

50% Sodium hydroxide (176 g, 2.2 mol) was added dropwise to a one-liter, three-necked flask containing a solution of hydroxylamine hydrochloride (153 g, 2.2 mol) in water (230 g)while maintaining the temperature below 35° C. with a water cooling bath. To the resulting mixture containing hydroxylamine base was added CPCA (98% assay, 140 g, 1.96 mol) over a period of 5 min. Upon completion of the CPCA, the mixture separated into two phases. GC analysis showed that formation of CPCA oxime was complete. The upper organic phase was separated and from the aqueous layer for use in the second step of the process.

Formic acid (95%, 77.5 g, 1.6 mole) was added to the organic phase and the resulting mixture was refluxed (110°–120° C.) for 3 hours. The mixture was cooled to room temperature and 50% sodium hydroxide (128 g, 1.6 mol) was added while maintaining the temperature below 50° C. The resulting crude product mixture separated into two phases. Analysis of the organic phase (132 g) showed that it contained 88.36% (116.64 g) CPCN. The aqueous phase was extracted with t-BuOMe (35 g) to give 32 g solution (contained 6.87% CPCN) which contains 2.20 g CPCN. The total yield after work up was 118.84.14 g CPCN (90.5% of theory). Distillation of the combined organic phases gives CPCN having a purity of greater than 99% Based on GC analysis, the total amount of by-product cyclopropanecarboxamide formed was 3.48 g which demonstrates that the selectivity of the conversion of CPCA to CPCN compared to the conversion of CPCA to cyclopropanecarboxamide is 97.74%.

COMPARATIVE EXAMPLE

CPCA (99% assay, 7 g, 0.1 mol) was added to a 250-mL, three-necked flask containing formic acid (95%, 100 g, 2.07 mol) and hydroxylamine sulfate (9 g, 0.13 mol). The resulting mixture was refluxed at 110° C. for 30 minute. The reaction mixture (114 g) was cooled to room temperature and GC analysis showed that all of the CPCA has been consumed and only 2.03 g (39% yield) CPCN had been produced. Other products produced included chlorobutyronitrile 4.23 g (40% yield), cyclopropanecarboxamide 0.99 g (11.7% yield) and cyclopropanecarboxylic acid 0.66 g (7.7%). This example represents substantially the procedure described by Olah and T. Keumi, Synthesis 1979, 112.

The invention has been described in detail with particular reference to preferred embodiments thereof, but it will be understood that variations and modifications can be effected within the spirit and scope of the invention.

I claim:

1. Process for the preparation and separation of cyclopropanecarbonitrile (CPCN) by the steps comprising:

(1) reacting cyclopropanecarboxaldehyde (CPCA) with hydroxylamine base in the presence of water to obtain CPCA oxime, wherein the mole ratio of CPCA:hydroxylamine is about 1:0.5 to 1:5;

(2) contacting the CPCA oxime of step (1) with formic acid to obtain CPCN, wherein the mole ratio of formic acid:CPCA oxime is about 0.5:1 to 5:1; and (3) contacting the mixture comprising CPCN formed in step (2) with a base to obtain a mixture comprising an organic phase containing CPCN and an aqueous phase, wherein the equivalents of base per mole of formic acid used in step (2) is in the range of about 0.5:1 to 2:1.

2. Process according to claim 1 wherein the base in step (3) is selected from the alkali metal hydroxides and carbonates and the alkaline earth metal hydroxides and carbonates.

3. Process according to claim 2 wherein step (1) comprises the use of an aqueous solution of hydroxylamine base containing about 10 to 50 weight percent hydroxylamine and the removal of water by distillation at the end of step (1).

4. Process according to claim 2 wherein step (1) comprises the use of an aqueous solution of hydroxylamine base generated in situ by contacting a solution of a hydroxylamine salt with a base and the separation of an organic phase containing CPCA oxime from an aqueous phase.

5. Process for the preparation and separation of cyclopropanecarbonitrile (CPCN) by the steps comprising:

(1) reacting cyclopropanecarboxaldehyde (CPCA) with hydroxylamine base in the presence of water at a temperature of less than about 120° C. to obtain CPCA oxime, wherein the mole ratio of CPCA:hydroxylamine is about 1:1 to 1:1.2;

(2) contacting the CPCA oxime of step (1) with formic acid at a temperature of about 50° to 150° C. to obtain CPCN, wherein the mole ratio of formic acid:CPCA oxime is about 0.7:1 to 3:1; and (3) contacting the mixture comprising CPCN formed in step (2) with an aqueous solution of an alkali metal hydroxide at a temperature of less than 75° C. to obtain a mixture comprising an organic phase containing CPCN and an aqueous phase, wherein the equivalents of alkali metal hydroxide per mole of formic acid used in step (2) is in the range of about 0.8:1 to 1.2:1.

6. Process according to claim 5 wherein step (1) comprises the use of an aqueous solution of hydroxylamine base containing about 10 to 50 weight percent hydroxylamine and the removal of water by distillation at the end of step (1); step (1) is carried out at a temperature of about 5° to 80° C.; step (2) is crried out at a temperature of about 80° to 120° C.; and step (3) is carried out at a temperature of about 30° to 55° C.

7. Process according to claim 5 wherein step (1) comprises the use of an aqueous solution of hydroxylamine base generated in situ by contacting a solution of a hydroxylamine salt with a base and the separation of an organic phase containing CPCA oxime from an aqueous phase; step (1) is carried out at a temperature of about 5° to 80° C.; step (2) is crried out at a temperature of about 80° to 120° C.; and step (3) is carried out at a temperature of about 30° to 55° C.

8. Process according to claim 5 wherein the aqueous solution of an alkali metal hydroxide is 50 weight percent sodium hydroxide solution.

* * * * *